(12) United States Patent
Jensen

(10) Patent No.: US 6,866,509 B2
(45) Date of Patent: *Mar. 15, 2005

(54) DENTAL DIAGNOSTIC SYSTEM AND METHOD

(76) Inventor: Charles D. Jensen, 7601 Lewinsville Rd. Suite 100, McLean, VA (US) 22102

( * ) Notice: Subject to any disclaimer, the term of this patent is extended or adjusted under 35 U.S.C. 154(b) by 177 days.

This patent is subject to a terminal disclaimer.

(21) Appl. No.: 10/263,881

(22) Filed: Oct. 4, 2002

(65) Prior Publication Data

US 2003/0044755 A1 Mar. 6, 2003

Related U.S. Application Data

(63) Continuation-in-part of application No. 09/635,531, filed on Aug. 9, 2000, now Pat. No. 6,491,522.

(51) Int. Cl.$^7$ ................................................. A61C 5/00
(52) U.S. Cl. ......................... 433/215; 433/27; 600/590
(58) Field of Search ............................. 433/27, 28, 32, 433/215, 216; 600/590, 300

(56) References Cited

U.S. PATENT DOCUMENTS

| | | |
|---|---|---|
| 3,753,434 A | 8/1973 | Pike |
| 3,916,529 A | 11/1975 | Mousseau |
| 4,302,627 A | 11/1981 | Inoue |
| 4,353,693 A | 10/1982 | Dery et al. |
| 4,526,179 A | 7/1985 | Salesky |
| 4,537,573 A | 8/1985 | Sunada |
| 4,641,089 A | 2/1987 | Pearman et al. |
| 4,676,257 A | 6/1987 | Halpern |
| 4,790,751 A | 12/1988 | Reinhardt et al. |
| 4,955,810 A | 9/1990 | Levy |
| 4,960,132 A * | 10/1990 | Habekost ..................... 600/589 |
| 5,049,069 A | 9/1991 | Salesky |
| 5,306,144 A | 4/1994 | Hibst et al. |
| 5,742,700 A | 4/1998 | Yoon et al. |
| 6,525,819 B1 * | 2/2003 | Delawter et al. ........... 356/406 |

* cited by examiner

*Primary Examiner*—Cary E. O'Connor
(74) *Attorney, Agent, or Firm*—Young & Thompson

(57) ABSTRACT

A dental diagnostic system for analyzing tooth structure, restorative materials within a tooth structure, and disease states of a tooth includes an analyzer which may be attached to a variety of dental probes, dental drills, and instruments to afford adaptability to a variety of clinical situations in providing diagnostic information on the naturally occurring tooth structure, man-made materials placed or found within the tooth structure, diseased or otherwise affected, infected or effected tooth structure, as well as tooth structure that has been eroded, worn by attrition, abraded, abfracted, fractured, crazed, broken or otherwise compromised through patient use, misuse, fatigue or longevity of use; and a method of diagnosing using the system.

20 Claims, 6 Drawing Sheets

DENTAL DIAGNOSTIC SYSTEM AND METHOD

This application is a continuation-in-part of Ser. No. 09/635,531, filed on Aug. 9, 2000, now U.S. Pat. No. 6,491,522.

BACKGROUND OF THE INVENTION

The invention relates to a dental diagnostic system and method for analyzing tooth structure, restorative materials within a tooth structure, and disease states of a tooth.

DESCRIPTION OF THE RELATED ART

Although there have been any number of changes in dental technology in recent years, just a handful of advancements have been in the field of electronic diagnostics. With regard to this burgeoning field, there have been some impressive additions. The advent of integrated circuits has allowed for complex circuitry to be designed that a scant thirty years ago was impossible.

For instance, Sunada, U.S. Pat. No. 4,537,573, entitled "Detector For Diagnosing Dental Caries", discloses that through the use of a hand held apparatus applying a 400 Hz signal, a dentist can jointly contact a tooth with a probe and watch the detector indicator lights, to find an indication of the quality of tooth structure.

U.S. Pat. No. 4,955,810 to Levy, entitled "Dentin Thickness Monitor" is similar to Sunada, but has a more complex electric circuitry that includes operational amplifiers, logic circuitry, and a host of discriminating LED's.

U.S. Pat. No. 3,753,434 to Pike, entitled "Electronic Device for Measuring Penetration Of Tooth Root Canal And Endodontic Therapy Method", is for the use of an electronic device for accurately determining the point of penetration of root canal and contacting periodontal tissue with a oscillating measuring signal.

Such systems are limited in that they are based primarily on detection of the precise end of a root, and as such as calibrated to determine when the dental instrument is within 3 mm from the end of the tooth.

Similar to Pike is U.S. Pat. No. 4,353,693 to Dery, entitled "Apparatus for the Determination and Digital Display of the Position of Root Treating Means in a Tooth," which device measures AC conductivity.

U.S. Pat. No. 5,049,069 to Salesky, entitled "Digital Apical Foramen Locating Apparatus with Linear Graphing," pertains to the endodontic specialty. Salesky teaches to recognize that the conductance from the apical foramen to a patient's lip is equal to the conductance from the sulcus to the lip and is further constant from patient to patient.

Root canal length measuring devices have also been disclosed in U.S. Pat. No. 3,916,529 to Mousseau, "Method of and Instrument for Determining Length of Root Canal . . ."

Transillumination, or the use of reflecting light through a tooth to determine decay, is disclosed by Hibst, U.S. Pat. No. 5,306,144.

These are all worthy of mention, but lack in full breadth and scope of what is possible now, and of what could be in the future. Electronics and electrical diagnosis in dentistry can be used to gather a much greater range of information through which a practitioner can make a more well-informed decision on treatment modalities.

Thus, in some regards, modern dentistry has become quite complex. Some aspects of dental technology have changed with improvements and greater acceptance of orthodontics, endodontics, advanced oral surgery techniques, and geriatric patients. These improvements, coupled with greater public awareness and public demand to keep their teeth, requires that the skills of dental practitioners continue to be enhanced.

Diagnostics is one such area in dentistry in which enhanced skills continue to be needed. However, the prior art has not been forthcoming in making diagnostic advances.

Take, for example, the main dental diagnostic tool, the common dental explorer or probe. This mainstay in dental technology for diagnosing caries, has not changed for 150 years. It is of the same design now as it was in the last century.

The prior art has recognized that teeth have a characteristic electrical conductance. P. Pincus described such findings in a publication of the "Proceedings of the Physiological Society," in the 15–16 Dec. 1951 issue. His paper and findings are entitled, "A New Method of Examination of Molar Tooth Grooves for the Presence of Dental Caries." He indicated that human tooth enamel consisted of 95% lime salt and is an extremely poor conductor of electricity, and that breaks in continuity might result from cracks, hairline fractures, developmental faults and non-calcified organic material.

The prior art has provided devices with visual and audible interpretation of treatment through which the operator may monitor the progress of the clinical case. However, the prior art have not gained wide acceptance and suffer from various problems, e.g., they show indicator lights attached directly to the head of the dental handpiece. This position for the lights turns out to be impractical. For example, repeated sterilization of the dental handpiece adversely affects indicator lights and renders the indicator panel non-functional in a rather short period of time.

In the prior art, when determining inter-proximal decay the dental practitioner has had to rely on x-rays or clinical examination to detect caries in these locations. Current methods of clinical examination include visualization and touch with the explorer. Both, however, can give false information. X-rays have been considered state of the art, but do not allow for early detection of incipient lesions. For example, leakage around the periphery of a filling can not always be checked adequately with these methods. Further, these methods have not always proved satisfactory as to ascertaining the quality of tooth structure in all types of cavities, including Class I, II, III, IV, V, VI, and some types not classified in these groups such as crown margin caries, and intracanal caries.

Although the current method of choice in dentistry to diagnose inter-proximal decay is with x-rays or radiographic interpretation, even given ideal circumstances, it has been shown that x-ray diagnosis is correct only about 30% of the time. Indeed, these methods are difficult for the inexperienced practitioner to achieve success as it generally requires years of clinical experience to master x-ray interpretation.

SUMMARY OF THE INVENTION

An overall objective of the invention is to provide a system and method which improves the diagnostic capability of the dental practitioner utilizing a single-multi-functional device.

Another object of the invention is to provide a system and method to supply adjunctive information by which the dental practitioner may make a better decision regarding treatment alternatives.

Yet another object of the invention is to provide a method of determining if teeth or tooth structure is cracked, from disease or overloading; locating perforations through a tooth during root canal therapy, or during restorative procedures; determining key locations to place pins so as to select areas that will minimize the chance of cracking the tooth, or to minimize the possibility of causing nerve damage; determining, once a pilot hole has been made, whether a frank opening into the nerve has inadvertently been made; testing sealants for leakage or decay; and identifying hidden pit caries.

Still another object of the invention is to provide a diagnostic analyzer device having a lead which can be attached to an instrument being used to treat the patent, without distraction to the treatment, and having a audible results output monitor through which the dental practitioner can hear decay being removed by providing a compactly sized device which has easy portability and direct attachment to an appropriate dental handpiece, a dental explorer, or other suitable intraoral dental instrument/probe.

In another respect, the invention has as an object to provide a system for establishing objective readings or findings which can be used as a baseline recorded in a patient's chart for future comparisons.

For a further object of the invention, there is the object of addressing a pulp exposure situation by providing a system and method of finding the approximate outline of nerve so that adequate nerve coverage is provided to prevent post-operative sensitivity.

The invention has as an additional object providing a device which can be used to help differentiate between enamel, dentin, sclerotic dentin, reparative dentin, thin or weak dentin, carious pulp exposures, iatrogenic pulp exposures, perforations, major canals, accessory canals, cracks, fissures, craze lines (and their length, direction and potential for problematic cause).

Another further object of the invention is providing a device and method of monitoring an isolated area, e.g., one that has been covered by a dental rubber dam.

A more further object of the invention is to provide a method to determine if a filling material, base or cement had been adequately cured or sealed, prior to conclusion of a treatment.

One more object of the invention is to obviate the need for x-rays and the such to diagnose interproximal decay.

The device of the present invention utilizes the principle that teeth and their associated structures behave like physiologic resistors. Although this basic premise is not newly discovered (as described by P. Pincus in 1951), it appears that the concepts have gone unnoticed or not fully exploited as of yet, by modern dentistry. There have been born certain concepts that have been implemented in dentistry, but these products fall short in being comprehensive and are not as all encompassing as this Dental Diagnostic Device and System.

Through familiarity with the use of the device, a practitioner would be able to analyze a myriad of dental conditions involving tooth structures, materials within a tooth structure, disease states of teeth, as well as to aid the practitioner in proper choice of methods of treatment of those conditions. A further realm of dentistry not yet completely investigated involves the science of materials. In conjunction with the use of the device, and specially designed materials, it would be possible to analyze materials before, during and after they are placed into teeth.

For instance, one source of post-operative sensitivity (after filling placement) is the incomplete setting of the materials. The practitioner may fully intend to cure or harden all materials placed into the teeth, but for reasons such as haste, poor maintenance of equipment, depth of cure and such, the material is left uncured in the tooth. Such material can cause sensitivity and lead to the removal of the restoration or worse yet, removal of the nerve, if the source of the sensitivity is not correctly diagnosed. It is possible to manufacture materials that conduct electricity while "wet" or as they are first mixed, and as they dry or harden, their electrical conductance decreases or resistance increases. It would be a simple matter for the dentist to check, with the device, each layer as it is placed and cured, to determine if the material has hardened. The readings from the unit would register low resistance and high audible readings when first mixed or placed, and would yield high resistance or low audible readings when completely set. It is then a matter of attaching an explorer or other dental probe to the device and testing various areas of the material just cured or hardened within the tooth. Such a test would require but a few seconds of time, but would assure the dentist of proper curing or hardening of the material. Hence, one potential source of patient sensitivity could be virtually eliminated.

Thus the present invention recognizes that modern dentistry, as a whole, owes much to previous ideas, invention and products, and should continue to strive for excellence in research and manufacturing, and lead the way in diagnosis, prevention, and treatment of dental disease. The present invention seeks to improve on the prior art and overcoming some of its disadvantages.

An overall objective of the invention is to provide an innovative and new approach to dental diagnostics, which supplements and improves the current diagnostic capabilities of the dental practitioner.

Another object of the invention is to provide a system and method to supply adjunctive information by which the dental practitioner may make a better decision regarding treatment alternatives.

Yet another objective of the invention is to aid the practitioner during treatment, to enable him or her to alter the course of treatment based upon information received from the system and method on a real time basis.

Still another objective of the invention is to enable the dental practitioner to correctly advise the patient of possible treatment outcomes as they become apparent, and to increase the chances for success given certain circumstances for which the system has been specifically devised.

The system and method can be used in the field of Endodontics (root canal therapy) to aid in the location of extra or missed canals during root canal therapy, or in determining if uninstrumented canals exist in light of post-operative sensitivity on previously completed root canals.

Still another objective of the invention is to determine the quality of an endodontic seal of the canals after completion of root canal therapy, given that certain materials can be manufactured with high resistance in a set state. These readings can be recorded in the patient's records for future reference.

Yet another objective of the invention is to aid the practitioner in determining if a dentinal plug is present within the canal or at the apex of the canal. Such information can reduce time spent in establishing correct working lengths, or patency of a difficult canal.

Another objective of the invention is to aid the practitioner in determining the precise location of a separated or broken instrument. Ordinarily, the tip of a broken endodontic file may be difficult to locate, and current methodologies suggest working around the small metal piece. However, with the system and method devised, the practitioner can locate the piece and decide whether to enlarge the canal and retrieve it, work around it, or decide that a proper seal of the apex has been established beyond the separated section, if no readings are obtained from the device.

Still another objective of the invention is to aid the practitioner in locating the direction or curvature of the apex of a root. It is possible to determine the sharp bend at the apex of a root by carefully interpreting the readings obtained while rotating the file in the canal. Hence, by determining the direction in which the canal courses, the practitioner may alter his or her treatment approach and obtain a better treatment outcome.

Yet another objective of the invention is to aid the practitioner in determining if a crack is present in or on a tooth. This is particularly useful since cracked teeth are usually lost due to their poor healing prognosis. With this extra information, the practitioner might be better prepared to advise the patient if treatment objectives could be met. If the crack is to be sealed, the practitioner may use specially designed cement that does not conduct electricity when set, thereby indicating that a crack has been adequately sealed. Current methodologies and standard of care require the removal of a cracked tooth. However, subsequent treatment for the replacement of the tooth removed require bridges, implant therapy and crowns, or replacement of the missing teeth with removable partial dentures, all of which require additional work and expense, and may have deleterious effects on the surrounding dentition.

The system can be used in restorative dentistry as well. It is possible for the dental practitioner to test and isolate the extent and outline of a nerve. By testing the areas within a tooth, the device will give readings that are closer to the nerve. By carefully walking the probe around the interior of the tooth, the operator can determine where a base should be placed in order to properly cover the nerve, thereby reducing the potential for post-operative sensitivity. Exposures of a tooth nerve can occur due to caries, operator error, nerve chamber morphology or shape that falls outside the bounds of normalcy that cause inadvertent entry into the nerve. Properly identifying the nerve size and shape may be critical in determining a proper course of treatment.

Still another objective of the device is to help the practitioner determine if the protective base is thick enough to aid in nerve protection. Once the pulp or nerve chamber is covered, the operator may test the area again to determine what, if any, readings are available. Adequate coverage might yield low readings where just previously high readings where obtained, indicating that the base material is protecting the nerve.

Yet another objective of the device is to indicate to the dentist what type of tooth structure is present. All types of tooth structures pass varying amounts of electrical flow. From this vantage point, the dentist may be able to determine if sound enamel or dentin is present, as well as to determine if sclerotic dentin, reparative dentin, dentinal bridges and other forms of dentin are present. This additional information may be of use to the practitioner in helping to determine a proper course of treatment.

Still another objective of the device is in aid to the orthodontist. The practitioner may use the device to determine if sound enamel exists on which to bond a bracket. Diagnosing poor quality enamel or filling material in the proposed location of bonding would help the dentist in judging if the site is acceptable. After the site is chosen, and the bracket is bonded, the orthodontist or general practitioner may periodically check the enamel around the bracket to determine if a decay process is occurring. In certain circumstances, improved oral hygiene technique by the patient would be necessary.

In consideration of the need to enhance future diagnostic equipment and treatment modalities in dentistry, the invention provides that changes could be readily made. Substitution of integrated circuitry, modifications in design to facilitate manufacture of a wrist-watch sized device, or the potential of using a wireless designed unit to transmit to a nearby base station or computer, could be easily worked into the basic design, and would change, little, the intent of the original device. Current apex locators on the market today, could in fact be altered quite readily, to improve them and achieve these basic objectives listed, but in fact would duplicate and thereby emulate this device. Adapting and modifying the device through the use of bipolar probes, using alternating current of varying Hertz, or even using separate signals that are subtracted or added, might be helpful, but would still allow the practitioner to diagnose and evaluate conditions of tooth structure and materials in a similar way as the device described.

A further objective of the invention is to act as a rudimentary pulp tester. As designed, it is possible for the operator to determine if local anesthesia has taken effect. Once tested with the device, if the patient indicates a sensation from the tooth, due to excitation of the neural component of the tooth or jaw, the practitioner may elect to wait several more minutes for the local anesthesia to take further effect, or he or she may opt to administer more anesthesia. It is possible to further improve the device by adding a variable resistor, or rheostat that will vary the amount of voltage entering the patient's tooth. With a voltage below 75 millivolts, the chance of causing neuronal stimulation, even on a non-anesthetized tooth, decreases. However, the phenomena or problem of "plurality of physiological resistor circuits," still remains.

Further objects and benefits of the invention will become clear from the following disclosure.

DESCRIPTION OF THE PREFERRED EMBODIMENTS

The invention recognizes that teeth are physiologic resistors and therefore conduct electricity. The enamel, the tough outer surface of the tooth, is the hardest naturally occurring material found in the human body and has just about an infinite resistance (in ohms). Dentin, the inner tooth structure, is also strong, but does conduct some electricity. Additionally, decay, cracks, nerve tissue, and reparative dentin all conduct electricity in varying quantities.

The resistance to electrical flow as an actual, measurable number is exploited by the invention to determine properties or conditions of a tooth being examined. Appropriate measurement yields tremendous information to the dentist. This information improves diagnosis, aids in better treatment, and allows for earlier detection of problems.

Preferred embodiments of the inventive dental diagnostic system include a stand-alone tooth condition analyzer as well as a tooth condition analyzer together with an auxiliary display. In some embodiments both the tooth condition analyzer and the auxiliary display will provide output indicative of the tooth's resistance and condition. In other embodiments, using the auxiliary display, the tooth condition analyzer need not have its own output device.

Figure 1:
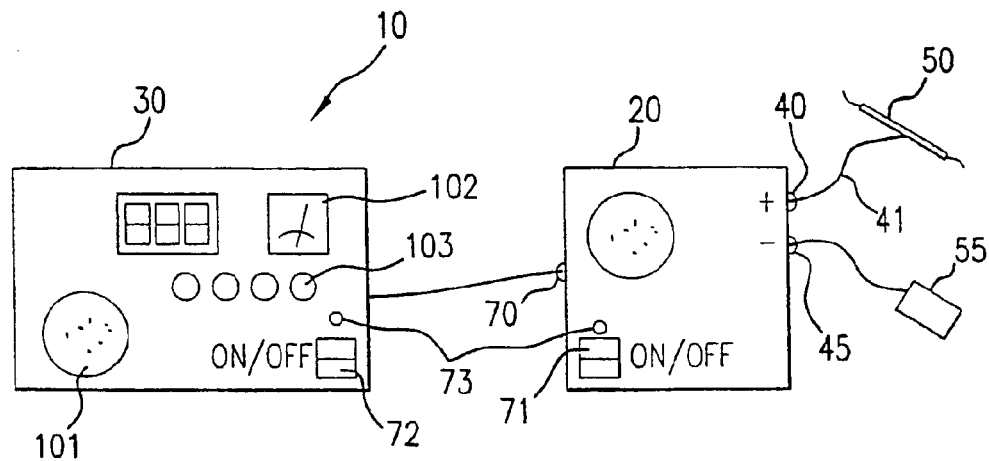
FIG. 1 shows the dental diagnostic system of the invention.

In FIG. 1 the dental diagnostic system 10 is shown with the tooth condition analyzer 20 with the auxiliary display unit 30 connected. In the figure both the analyzer and the auxiliary display have at least one output device; however, the particular selection and arrangement of output devices may be as desired. As noted above, when used with the auxiliary display, the analyzer need not have an output device.

Figure 2:
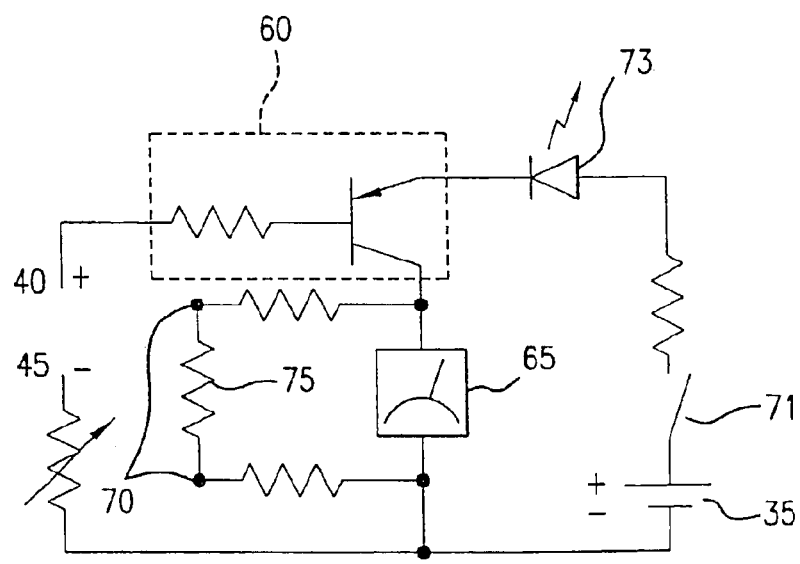
FIG. 2 shows one circuit layout for the tooth condition analyzer.

FIG. 2 shows one circuit for the tooth condition analyzer 20. Those skilled in the art will appreciate that alternative circuits having the disclosed characteristics are also possible.

The analyzer includes a DC voltage source 35. The DC voltage source may be a 4.5 volt DC battery. Via the analyzer circuitry, DC voltage is applied across a positive voltage terminal 40 and a negative voltage terminal 45. The positive terminal provides a connection terminal to a dental tool 50. The positive terminal also provides one of a known DC voltage and a known DC current onto the dental tool. The negative voltage terminal provides a connection terminal to a return connector 55 for completing a circuit from the positive voltage terminal via the dental tool then via a patient's tooth to the negative voltage terminal.

The return connector can take the form of a lip clip, a shoulder plate, or a hand-held connector. The lip clip is placed on the client's lip, the shoulder plate is placed in contact with the patient's shoulder, and the hand-held connector is squeezed by one of the patient's hands.

The analyzer further includes a voltage/current circuit 60 connected to the positive and negative voltage terminals and providing either a known DC voltage across the positive and negative voltage terminals or a known DC current therebetween.

A resistance indicating means 65 serves as an output device for indicating the resistivity appearing across the positive and negative voltage terminals, and by implication, of the patient's tooth. The indicating means is operatively connected to the positive and negative voltage terminals for sensing a current flowing therebetween and converting the current to a resistance indication or for sensing a voltage developed therebetween and converting the sensed voltage into a resistance indication.

From the above, one sees that either a DC voltage or a DC current is developed by the analyzer across the positive and negative voltage terminals. Maintaining either a known voltage or current is necessary in order to establish the tooth's resistance based on measuring the developed current or voltage being developed across the positive and negative voltage terminals, i.e., resistance of the tooth equals either a measured voltage divided by a known current or a known voltage divided by a measured current.

Further it is necessary to limit applied voltage and applied current in order to keep the patient safe and comfortable. The voltage/current circuit limits the current which can flow between the positive and negative voltage terminals to 300 microamps. When the patient is not anesthetized the voltage should be limited to no more than 70 millivolts. A greater voltage is possible when anesthesia is used.

Figure 3:
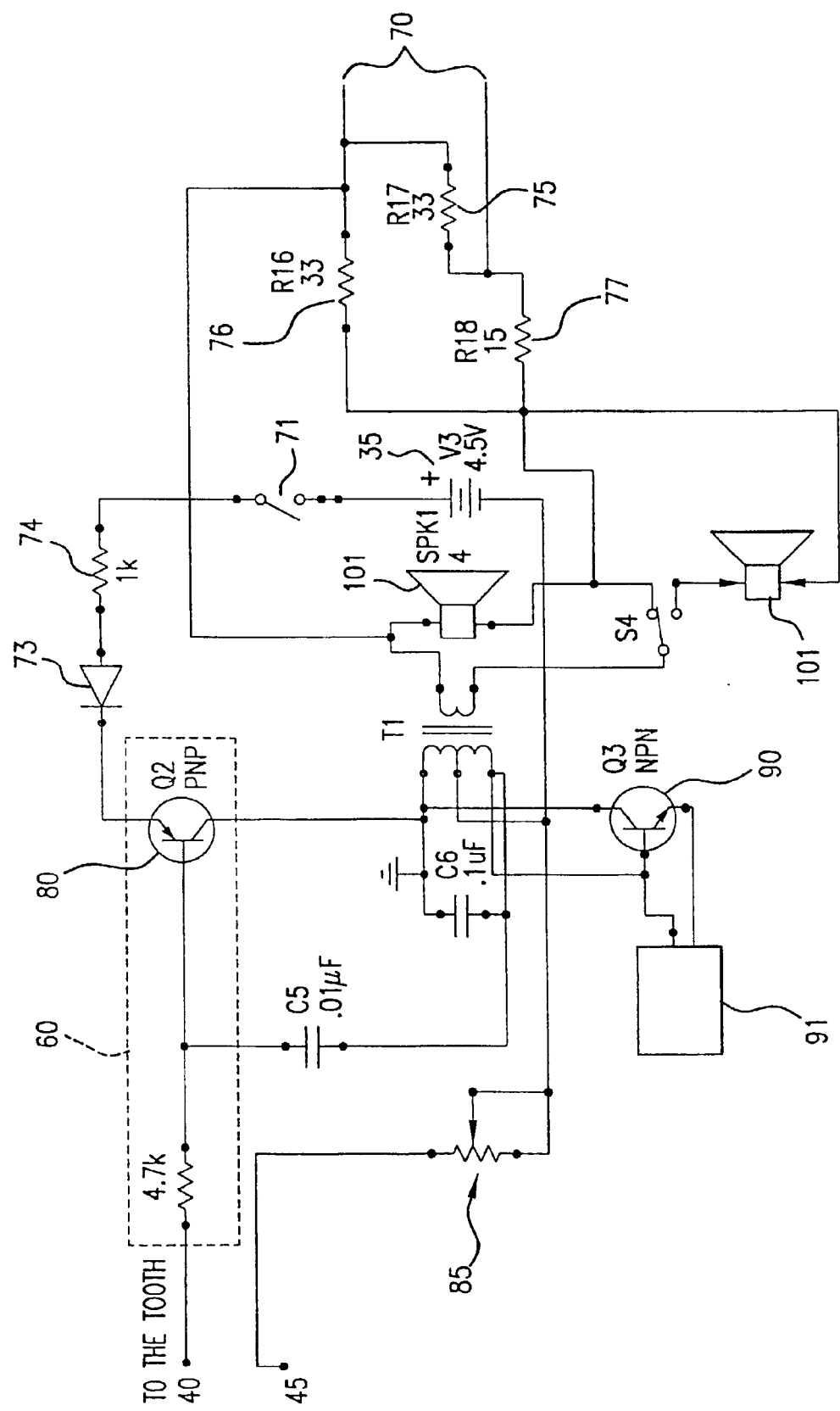
FIG. 3 shows another circuit layout for the tooth condition analyzer.

The power supplied to the analyzers of FIGS. 2–3 is used to test the tooth. This voltage is applied to the tooth and the resulting current (or voltage) is amplified so as to drive an output device such as a gauge 65 for visual display or a speaker 101 to yield audible diagnostic information. Optionally, headphones may provide audible output in addition to or in lieu of a speaker.

Further, the analyzer developer current is passed to auxiliary display which is connected in parallel with the analyzer by way of a voltage developed in a bridging resistor 75 (coupler) spanning a connection 70 between the two circuits.

Thus, the tooth condition analyzer may comprise an auxiliary load display connection 70 operatively sensing the resistivity appearing across the positive and negative voltage terminals. The auxiliary display is connectable to the auxiliary load display connection. The auxiliary display and the analyzer are independently powered and have separate power switches 71, 72. Each may have a power-on indicator 73.

Figure 4:
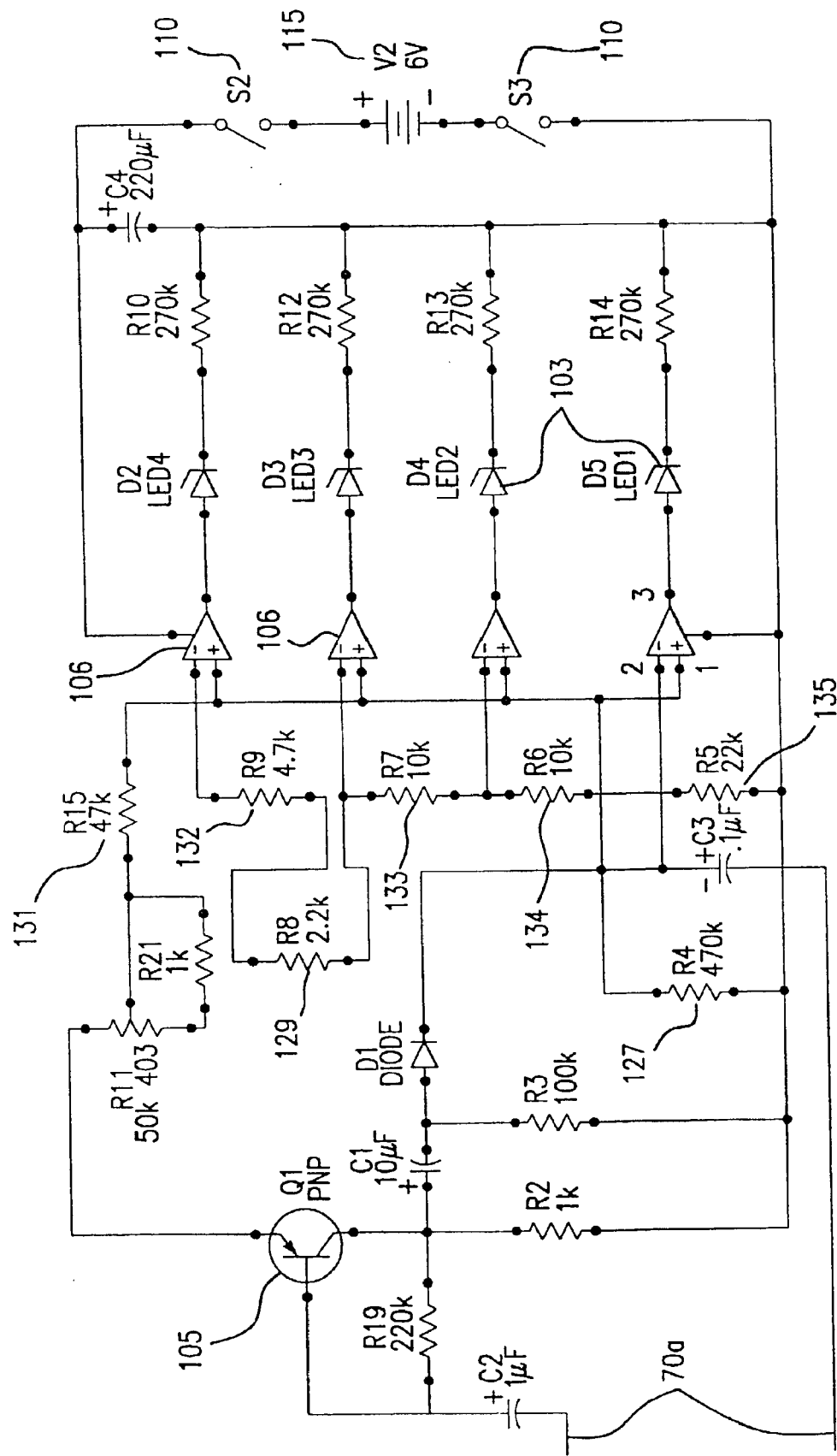
FIG. 4 shows one circuit layout for the auxiliary output display.

FIG. 3 shows another circuit layout of analyzer while FIG. 4 shows a circuit layout of the auxiliary display. These two circuits can be connected as shown by FIG. 1. Although these two circuits may be commonly joined by connecting connections 70 and 70a together, they have separate power supplies so that the auxiliary display does not load down the analyzer.

Another advantage of having two separate circuits includes giving the dentist flexibility to choose between additional display indicators such as a audible indicator 101, a gauge 102, or lights 103 located on the auxiliary display in addition to a audible indicator 101 which may be the only indicator on the analyzer. Various display indicators are shown by FIG. 1; however, various known displays including LCD and other digital displays are also possible.

The auxiliary display functions to amplify the voltage developed across the bridging resistor so as to drive one or more additional types of output. The auxiliary display output may comprise a set of LED's (light emitting diodes) 103 as shown.

Figure 5:
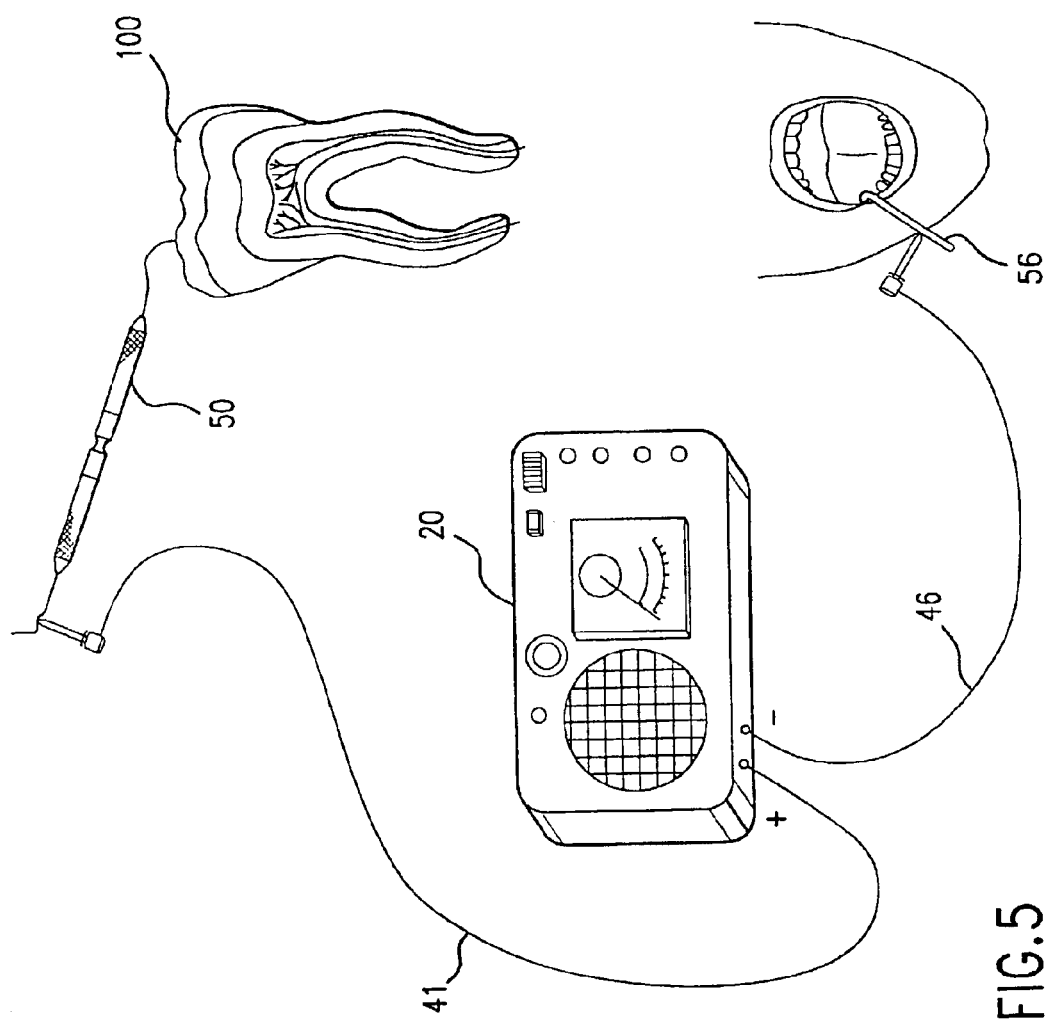
FIG. 5 shows the inventive system in use.
Figure 6A:
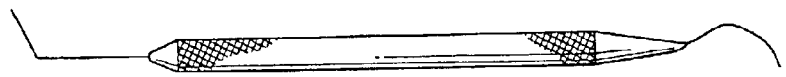
FIG. 6 shows dental tools that may be used with the inventive system.
Figure 6B:
Figure 6C:
Figure 6E:
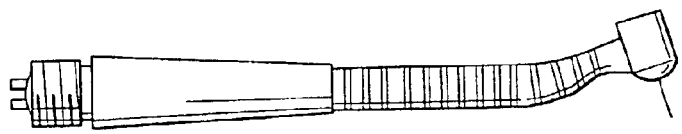
Figure 6F:
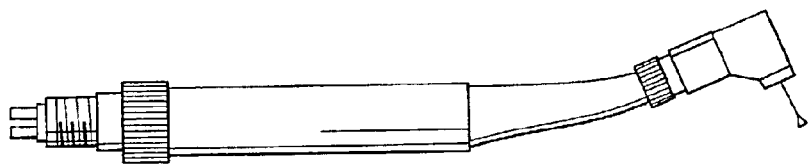
Figure 6D:
Figure 6G:
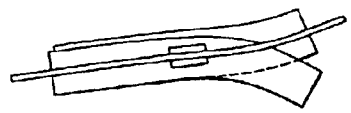

With reference to FIG. 5, the analyzer circuit works by sensing the voltage developed or current that flows when a lip lead 56 (negative side) is attached to the patient's lip or suitable ground, and the positive lead is attached to the dental tool 50 being used to contact and assess the patient's tooth 100.

The voltage is 4.5 V DC in the analyzer circuit of FIG. 3. This voltage may be varied; however, careful consideration should be used in selection of this primary voltage source, because applying a voltage which would result in an amperage of more than 30 milliamps could interfere with a patient's heart, or pace maker. The circuit of the invention should be maintained below such an amperage. Preferably, the voltage is selected to generate less than 300 microamps and more preferably between 30 and 300 microamps.

One PNP transistor 80 is used in this circuit to enhance and increase the measured current from the patient. The speaker 101, being 8 watts, cannot be driven with a voltage that is below its threshold, which is generally at the minimum of 1.5 volts.

A variable resistor 85 is used to help regulate the voltage through the circuit. One NPN transistor 90 is used to drive the gauge 91. The feed to transistor 90 comes from the collector of transistor 80. The speaker 101 changes the input signal, which is amplified through the transformer hooked to the speaker to yield an audible tone, which increases linearly as more current is fed through the tooth or object being tested and which returns from the negative lead hooked to the patient's lip. As the audible signal registers less resistance from the test subject, a higher pitch is realized.

Concurrently the gauge 91, which requires a boosted signal from transistor 90, yields a visible result on the dial. This allows a more objective evaluation of the audible reading and permits the operator to record the visual numbers in the patient's chart for future reference.

A variable resistor 85 is placed into the circuit to allow for some generalized modification of the voltage, but should work well with no adjustments. The light emitting diode (LED) 73 has been placed into the circuit as an on/off indicator light. It is quite possible to add to the circuit a system to alert the practitioner if the batteries are low in voltage. The voltage source 35, of 4.5 volts is controlled by a SPST (single pole single throw) switch 71, which without this switch would allow the circuit to leak voltage and drain the batteries.

Resistor 74 helps regulate circuit voltage levels.

With reference to FIG. 3, the coupler between the analyzer and auxiliary display comprises three resistors 75–77. This arrangement provides proper sensitivity and control of the loading of the auxiliary display onto the analyzer. This arrangement also obviates the need to provide a calibration or reference step.

The auxiliary display of FIG. 4 is used to drive the LED's. The voltage sensed from the bridging transistor 75 of the analyzer is directed through the auxiliary display circuit by diodes and resistors.

PNP transistor 105 steps up the sensed voltage; however, the majority of the amplification comes from the four low-power operational amplifiers 106. Alternatively, these four operational amplifiers could be implemented as an integrated circuit, e.g., using IC #BA1032A.

These four op-amps are attached in series, and depending upon the resistance detected within the tooth, varying numbers of the LED's light up. For instance, if a "short" were to occur by touching the probe to the patient's lip or tongue, all four lights would be lit. As more resistance is encountered the number of lit lights goes from four, to three, to two, and then to just one light.

Thus, if just one light is lit, then the resistance of the tooth would be high, and permit just a trickle of current through the tooth, and back into the device by way of the grounded lip lead.

As noted previously, the auxiliary display is driven by its own power source to help stabilize the voltage driving the circuit by avoiding the auxiliary display from becoming a significant load to the analyzer as voltage drops or fluctuations in analyzer battery strength may cause erratic readings. Two switches 110 are used in the circuit to help the voltage source from bleeding off while the circuit is not being used. The voltage source 115 for the auxiliary display is also modest, e.g., 6 volts DC.

The Light Emitting Diodes used to reflect measurements are described as follows. LED #1 is green in color, and when it is the only one lit, indicates low current flow through the tooth and thus indicates good tooth structure, with high resistance to voltage/current flow. LED #2 is yellow in color, and alerts the operator that the tooth in question allows a moderate amount of current. LED #3 is red, and would indicate very poor tooth structure, or close proximity to a nerve or crack. The operator would continue the work, until the reading is low enough to light only the green LED #1, or perhaps the green and yellow lights. At this point the practitioner might elect to stop work.

LED #4 is red, as well, and primarily indicates a "short" in the system. This might be in the form of a wet tooth or short through the practitioner hands.

Several resistors have been used to ensure that the bank of lights will be lit up gradually and remain lit for easier viewing. The steady gradation of lights was chosen to aid the practitioner visually. If a threshold is reached, the lights will be activated one by one, to exhibit the condition of the tooth being tested. To control the voltage allowed to enter each operational amplifier, a combination of parallel and series linked resistors are used 127, 129, 131, 132, 133, 134 and 135.

FIG. 6 shows various dental tools which may be used with the analyzer. The dentist may choose to use a dental explorer 6A, an endodontic explorer 6b, a spoon excavator 6c, an endodontic file 6d, a high speed dental drill 6e, a slow speed dental drill 6f, or an interproximal point conducting mylar strip 6g.

The positive lead 41 can be attached to any other conducting instrument of the practitioner's choosing, if the following parameters are observed. The attachment must be able to conduct electricity and hence, insulators with high resistance's cannot be used; a smaller, handheld type of lead can be manipulated much easier than large objects, due to the limited size of the working space found inside the mouth; care must be taken so as not to short the circuit by touching the probe to the cheek, gum tissue, soft or hard palates, saliva, lips, the (negative) lip lead 46, a wet glove in contact with any of these items mentioned, holes in the gloves, or gloves that are so thin as to allow electricity to pass through them. The lead and the device are versatile enough so that there can be many more leads, or types of leads that are not specifically stated in this embodiment, but implied due to the general nature of conducting instruments. In addition, metal instruments are capable of holding a small electrical charge, like a battery, and can discharge when they come into contact with a tooth, filling, or tooth with a more "lively" nerve.

Routine discharge the electrostatic buildup by touching the instrument to a suitable ground prior to contacting the patient is desirable. This practice is helpful in maintaining a patient's comfort. Patients might say "ouch" when at the first touch of a tooth if the instrument is statically charged, but by discharging static the instrument will no longer act to cause patient discomfort.

The ground lead 46 is shown used with a simple lip clip 56. However, any good contact with the patient can be made, including (but not limited to) the patient holding the negative lead in the hand, or by placing a metal plate 55 under the shoulder of the patient with good contact against the skin. Care must be taken to avoid any injury to the patient's, as a result of the use of said device.

As noted, voltage over 70 millivolts can cause rapid depolarization of the nerve membrane and cause pain to the patient. It is recommended that anesthesia (lidocaine or marcaine) be administered to the patient, and adequate time be given to allow for the anesthesia to soak in and produce the desired numbing effect. Insufficient anesthesia can be observed and can aid the practitioner in evaluating the level of anesthesia. Care should be taken so as not to attempt to hurt or "torture" the patient (See the movie "Marathon Man" with (patient) Dustin Hoffman and ("dentist") Sir Laurence Olivier, Paramount Picture, 1976).

Patients with a cardiac pacemaker would not be selected as patients to be treated with this device, due to the risk of causing the patient to go into fibrillation. Obviously, any change in heart rhythm could have a negative effect. The chance of this occurrence is very low and there are countless articles available that would seem to confirm the very low possibility of harming such a patient. The low voltage DC voltage 35 (of 4.5 volts) found in the analyzer, and voltage 115 (of 6.0 volts) found in the auxiliary display, yields a small amperage of 30 microamps This low amperage is not only below the recommended limits, but comes in at a magnitude ten times lower than the recommended maximum. Nonetheless, the patient should be monitored during treatment.

The invention can be used to obtain the following readings by testing certain areas of the teeth:

| COMPONENT STRUCTURE | RESISTANCE IN OHMS |
|---|---|
| Intact enamel | 600K or greater |
| Enamel (suspicious) | Less than 250K |
| Dentin 4 mm thickness | 500K or greater |
| Dentin 2 mm thickness | 230K |
| Dentin 1.5 mm thickness | 200K |
| Dentin 1 mm thickness | 150K |
| Dentin 0 mm | 80K |
| Pulp Tissue | 12K |
| Body's Resistance | 7K |

To reiterate, with the readings listed below, the practitioner can infer the following:

| OHMIC VALUE | DIAGNOSIS |
|---|---|
| Infinite | No caries/intact enamel |
| Greater than 600K | No caries |
| 599K–251K | Caries into dentin, or crack into dentin |
| 250K–15.1K | Caries of moderate to extensive quantities |
| Less than 12K | Pulp exposure due to decay, or drilling too deep, etc. |

The present system gives information that would correspond to the condition of the tooth in the following manner:

| DIAGNOSIS | AUDIBLE READING | GAUGE READING | LED READING |
|---|---|---|---|
| Tooth intact | None | Zero | None/Green |
| Pit caries just through enamel | Low | <1 (on scale) | Green or Green-Yellow |
| Shallow caries | Low–Medium | 0.5–1.5 | Green-Yellow; G–Y–Red1 |
| Moderate to deep caries | Medium–High | 1.5–2.5 | G–Y–Red1–2 |
| Very deep Caries | High–Very High | 2.0+ | G–Y–Red1–3 |
| Pulp exposure | Very High | 2.5+ | G–Y–Red1–4 |
| Short | Very High | 3.0+ | all LEDs |

| DIAGNOSIS | AUDIBLE READING | GAUGE READING | LED READING |
|---|---|---|---|
| OTHER FINDINGS: | | | |
| Crack through enamel | Low–Medium | 0.5–1.5 | Green-Yellow |
| Moderate crack | Medium | 0.5–1.5 | Green-Yellow G–Y–Red1 |
| Deep crack into nerve | High–Very High | 2.5+ | G–Y–Red1–4 |
| Deep crack through tooth | Very High | 2.5+ | G–Y–Red1–4 |
| Perforation through tooth or root | Very High | 2.5+ | G–Y–Red1–4 |
| Endodontic canal | High–Very High | 2.0+ | G–Y–Red1–4 |
| Accessory canal | Very High | 2.0+ | G–Y–Red1–4 |
| Missed canal | Medium–High | 1.0–2.0+ | G–Y–Red1 |
| Dentinal Plugs (apex) | Low–None | 0.25 | Green or G–Y |
| Pin Site (location) | | | |
| >2 mm from nerve | Medium | 0.5–1.5 | Green-Yellow or G–Y–Red1 |
| <2 mm from nerve | High | 1.0–2.0 | G–Y–Red1 |
| 0 mm from nerve | Very High–Short | 2.0+ | G–Y–Red1–4; or all LEDs |

These values are illustrative for the disclosed circuits. Similar systems can be adapted by this disclosure including digital direct readout of resistance valves, textual readout based on resistance valves, etc.

In an embodiment of the method of the invention, a dental treatment includes exploring a tooth surface 100 with a dental tool 50, with the dental tool applying a known DC voltage to various localized regions of the tooth surface area to locate a treatment area as indicated by a local low resistance area surrounded by a higher resistance area. This low resistance treatment area may be an area of decay.

After providing appropriate treatment in this area to remove the decay, successful treatment is verified by re-applying the known DC volt, via the dental tool, to the same treatment area and observing an increased resistance in the treatment area. The removal of the decay is indicated by the increased resistance in the treatment area, or in other words, is confirmed by the absence of the local low resistance area.

A dentist using the inventive method would take a medical and dental history. Note, the use of the inventive device and is contraindicated if the patient wears a cardiac pace maker.

After the patient's case is analyzed, it is determined at which point during treatment the device can be used diagnostically. In embodiments of the device which apply less than a 70 mvolt DC signal, local anesthesia may not be necessary as such low voltages should not stimulate any nerve impulses which would cause the patient pain. However, anesthesia may be indicated and administered in an appropriate manner.

The tooth area to be tested can be isolated with cotton rolls or the use of a rubber dam can be considered. In preparation of examination of the tooth, the negative lead from the device is attached to the patient's lip by the aid of a bent wire connector serving as a return contact. This wire connector provides contact with the moist oral environment, and allows for completion of the circuit. In lieu of the lip clip, one may elect to use other suitable means to contact with the patient's skin. For example, alternative return contacts may include a metal plate under the shoulder of the patient, in or a hand-held clip that the patient grasps in either hand.

The positive terminal lead 41 is then attached to the dental instrument of choice. The type and style of the instrument can be of the operator choice and could be, for example, any one of the following:

dental explorer, restorative or endodontic;

endodontic file;

dental drill, high or slow speeds; and spoon excavator.

The device is set to the "on" position, and once the appropriate point during treatment is reached, the device can be used by the operator to obtain information about the tooth and its properties by bringing the dental instrument into contact with the tooth surface and observing the measured resistance.

Contact with the dental instrument can be made to various parts of the tooth, and in general, it is the amount of DC current that passes through the tooth, into the jaw of the patient, and returns to the device via the lip clip or negative lead or return contact, that allows the device to indicate the results.

The sensing circuit receives the current from the test subject, the patient. Applying a test DC voltage to the patient that is less than 350 mvolts, preferably no more than 70 mvolts, and most preferably in the range of 20 to 40 millivolts is used limited the amperage passing through the patient to about 300 microamps. A maximum test current through the patient of 300 microamps (0.3 milliamps) provides a safety factor below the 30 milliamp threshold that could interfere with the electrical conductance of the heart.

As noted, the measured current indicated the resistance of the tooth and thereby the condition of the tooth. The measured current can by converted to a measurable voltage, e.g., by passing through a resistor or influencing a transistor. In embodiments such as FIG. 3, the developed voltage in turn may be stepped up through a transistor and/or a transformer.

The monitoring device is independently powered from the display module to assure safe testing of the patient. The display module indicates the tooth's condition by one or more conventional display means. These may include a digital readout of resistance, bar displays indicating tooth quality, a speaker, plural LEDs indicating tooth quality, and analog gauges.

In the case of a bank of LEDs such as shown in FIG. 4, the LEDs are lit in reference to the amount of voltage developed from the measured current returning from the test subject. An integrated circuit senses the voltage and lights the LEDs according to the voltage developed. The reference lights include one green light, one yellow light and two red lights where the green light corresponds to a low developed voltage (high resistance tooth area), the yellow light corresponds to a less resistance tooth area, and the red lights correspond to low resistance or tooth areas of concern.

In the inventive method, the operator can use any of the output types to help in diagnosis of the tooth and the test subject. With a speaker output, the speaker volume and tone can be interpreted, and will give a very general guideline as to the potential findings. If the speaker emits a low or weak tone, the tooth and its components tested would be considered to be intact, due to a higher resistance. As the speaker volume increases, the operator ascertains that the area being tested might be questionable, and could be interpreted as poor quality tooth structure, decay, a crack and the like. An extremely high speaker tone and volume, at a "blaring" level, would indicate a pulp or nerve exposure, extensive decay, perforation through the tooth, an extra or accessory canal associated with root canal therapy, and the such.

A gauge may have a range of 0–10 (unmarked units) and may be read and interpreted as follows: 0–5 normal tooth structure, 5–9 proceed with caution, the site being evaluated may be of questionable quality or may contain decay, 9+ would indicate a very low resistance and as such might indicate decay, a crack through the tooth, a perforation through the tooth, accessory canal, pulp exposure and the like.

Once the tooth's situation has been assessed, the operator would then react to the reading by continuing with dental treatment appropriate to the situation. During initial treatment, the operator would then retest the tooth as a next point in the treatment, and make an evaluation again based upon those findings or results.

As with any diagnostic device, the present invention is a diagnostic aid and it is imperative for the operator to grasp the basic concepts of the device, since the readings, like any diagnosis in medicine, require a good grasp of working knowledge, intuitive and deductive reasoning, careful interpretation of results, and follow up on treatment to verify successes or failures.

The operator will find that moving the dental tool across the exterior surface while observing for a change in audible tone of the speaker or a yellow or red LED light to become activated, will indicate a change in the resistance or quality of the tooth or area of the tooth being tested. Such a change when testing the enamel or root structure of the tooth would indicate a crack in the structure. Other possible causes for a change in the resistance of the tooth might mean decay, thinned enamel, leakage of a filling, marginal breakdown.

In the case of a crack, the solid enamel is the hard outer casing of a tooth and normally has a very high resistance, greater than 650K ohms. For all intents and purposes, this is an infinite resistance. This means that under ideal circumstances, enamel will not allow electricity to flow through it.

However, if the enamel has a crack through it, moisture, debris, bacteria, foodstuffs and the like will invariably be found in the crack. This "moisture" will allow for the transmission of electrical current through the enamel. The amount that travels through the enamel, through the tooth and patient's body, and through the negative lead, will be measured and indicated by the device.

There are several types of cracks that may be observed. Superficial cracks, located in the enamel and labeled as craze lines may be of no consequence, and would give only very low audible readings, or none at all. Cracks that have penetrated through the enamel and into the dentin will show up as low to moderate audible readings, or as one green and one yellow light. Cracks that have become large enough so as to be labeled as fracture, may course one of several directions: a short distance into the dentin, into the dentin and back out through the enamel, or into the nerve. Each of the situations would yield a very high audible reading, as well as one or two red lights. Cracks into the nerve or ones that exit back out through the enamel would be noted to cause "shorting" of the unit due to tooth presenting a very low resistance to the applied voltage, and hence would yield the highest audible readings.

The inventive method also includes use of the device by touching the dental probe to the tooth interior while observing changes in indicated resistance (voltage developed or current flow induced) of the tooth structure to locate perforations through a tooth during root canal therapy or during restorative procedures.

In such situations, the practitioner is working within the tooth, and when a reading is taken, a perforation or hole through the tooth may be noted by a very high audible reading, or by the illumination of 3 or 4 of the LEDs, i.e., indicated by low tooth resistance or low resistance paths with the tooth.

The perforation, if caused by the practitioner, would be noticed in a small vicinity. The perforation may not have been caused by the practitioner, and may, in fact be an extra canal in the root system. A fractured root may appear as a perforation since both represent a confluence with the exterior of the tooth, i.e. the bone and surrounding tissue.

The device may further be used in determining key locations to place pins so as to select areas that will minimize the chance of cracking the tooth or to minimize the possibility of causing nerve damage by identifying areas that come in close proximity to the nerve chamber, or the exterior of the tooth. In circumstances that require the placement of a pin into the tooth structure to aid in retention and resistance form of the filling, the device can be used to test the potential viability of a location by indicating how close to the nerve or the exterior of the tooth the chosen spot is located. Low resistance readings indicate less than 2 mm from a potential source of problem.

Generally, the placement of a pin into thin tooth structure in close proximity of the exterior of the tooth generates a greater risk for cracking of the remaining thin tooth structure. In addition, such areas represent a higher risk of actual perforation through the remaining tooth structure into the area surrounding the tooth. A perforation of this type might act to compromise the restoration. Similarly, if a pin is placed in close proximity to a nerve, ensuing nerve trauma or damage may result. Direct perforation of the pin into the nerve increases the risk of irreversible nerve damage that might necessitate root canal therapy.

If such potential sites can be identified as being good or bad based on indicated resistance, then the chances of restorative success can be increased, with a corresponding decrease in iatrogenic problems (errors caused by the operator).

In a device having an audible output, low readings via low audibles can be interpreted as indicator of good locations for pin placement as these indicate high resistance regions.

In ascertaining an approximate ideal location for pin placement, the operator initially uses the device to help indicate that the chosen location is of adequate distance from the nerve or the exterior of the tooth. After making a pilot hole for the pin using the appropriate drill bit, and of a depth recommended by the manufacturer, the operator again uses the device to determine if a frank exposure of the nerve has occurred, or if a perforation to the outside of the tooth has occurred by retesting the site with the device. Very high LED readings and audibles may indicate potential problems (low resistance).

Care should be used to assess the pilot hole, and if a problem exists, it may be recommended to cover the pilot hole with a base or cement and to determine if a new location should be sought out, tested and used. Advantageously, the invention allows a dentist to, in advance, advise the patient that a potential nerve problem may arise at some point in the future.

Sealants may be tested for leakage or decay by assessing the occlusal, buccal or lingual surfaces. Initially, one would clean the surface of the tooth, e.g., with pumice, wash, and dry the tooth with a 15 second blast of dry air. The dental probe is then placed into the groove, pit, fossa or other anatomical area in question. These areas in question may be suspected of decay due to their stained appearance, "stick" from a dental explorer, or as prelude to the normal and routine application of the sealant material to verify intact enamel.

Areas that yield medium to high audibles or red LED indicator lights, must be suspected of having outright decay, and may require fillings in lieu of sealants. However, areas that yield no or very low readings have intact enamel, and can be sealed, in lieu of having to drill these surfaces and place fillings.

Likewise, teeth that currently have sealants on them can be tested for leakage around the sealant in a similar fashion. The operator may test these areas and medium to high readings or audibles indicate leakage and potential decay under the sealant. It would then be recommended to remove the sealant and clinically observe and retest the areas in question. Upon retesting, if questionable readings are still noted, the tooth may be in need of a filling in lieu of an additional sealant.

In addition to locating major surface problems, the device may be used to detect hidden caries and/or pit caries. Such dental caries can be difficult to locate, identify, diagnose, remove or treat. Dental caries can be located in out of the way locations such as in dental pits or grooves, under existing restorations, or in areas hidden by tooth structure such as internal cuspal decay.

The device can be used to locate such decayed areas by testing the resistance to electrical flow, provided the operator use a dental probe or tool capable of coming into direct contact with the area in question. The probe can have a straight or bent or curved tip, which would aid in facilitating direct probing of the spot in question. In treatment, the device can be used for locating residual etchant by touching the probe to various areas after rinsing and drying. Etchant, as a conductor and providing a low resistance area, would yield an audible reading.

The invention in addition to locating caries, is useful in the extent and depth of any decay. As described above, one would conventionally isolate the tooth with cotton rolls, or rubber dam, and apply a strong blast of air for 10–15 seconds. Placing the first lead, i.e., the negative lead, to the patient's lip, and attaching the second lead, the positive lead, to an appropriate dental probe, the device is ready to apply a low known DC voltage to the tooth. Touching the area of tooth to be tested, the tooth is evaluated.

The application of the probe to a silver filling will yield low resistance results because the amalgam filling acts to amplify the signal as in a parallel circuit being formed. Thus, the best results occur when the probe is touched to natural tooth structure.

If done on virgin caries, or immediately after a failed filling is removed, reliable readings can be obtained. Once again, if high audible readings or activation of multiple LEDs are noted, then the interpretation can be one of several possibilities. The most likely is decay. Higher readings would indicate closer proximity to a nerve. Low readings would indicate shallow decay. "Shorting" or very high readings may indicate a pulp or nerve exposure, or perforation through the tooth.

The invention may avoid the use of x-rays when determining interproximal or approximal decay. Local anesthesia is administered to the patient and the area to be tested is isolated with cotton rolls or rubber dam. After a semiconducting mylar strip (FIG. 6G) is placed in between the teeth, the first and second leads are attached to the patient as previously described.

The semi-conducting strip can be fabricated as follows:

1. two identical mylar or plastic sleeves, commonly used in dentistry to rebuild teeth, can be glued together, after having cut a small window into one of those sleeves;

2. the window should be 2 mm×2 mm, and is positioned such that a small metal conducting strip placed in between the cemented strips is exposed;

3. the exposed metal conducting strip can be placed so as to be in contact with the tooth in an interproximal (in between the teeth) position.

The mylar strip should be positioned so that the metal conducting strip contacts portions of the tooth which are otherwise not accessible and so that a first portion of the metallic strip contacts any tooth surface which requires examination. By bringing the examining tool into contact with a second portion of the metallic strip, any low resistance areas of the tooth contacting the first portion are detected and further required evaluation can be determined.

Thus, if there is a break in the enamel located in between two teeth, and the device is attached in the standard way, current will be able to flow through the broken enamel via the metallic strip to the explorer or other tool connected to the device. Readings can be interpreted in a similar manner to other tests, with high audible readings indicating that the break into the enamel leads to decay. Conversely, if no audible readings are obtained, and the device is found to be working properly, then it can be ascertained that this interproximal tooth structure is secure, i.e. enamel, is intact and not broken.

Carious pulp exposures can also be detected by the present invention. Again, the practitioner would consider the administration of local anesthesia to keep the patient comfortable and the isolation of the tooth by cotton rolls or rubber dam. Air drying of the tooth prior to commencement of the work is recommended.

Testing should be of an area of the tooth which would be considered "virgin"; this is, an area which had never been drilled upon before. Otherwise, if a filling does exist, then it should be removed, and the tooth can be tested at this point, to determine the size and extent of the decay.

Alternatively, testing the tooth may be done by drilling a small hole (access opening) through a filling, crown, enamel, plastic or other material on the chewing or occlusal surface. This will allow for access to the tooth structure under the filling, and hence one would be able to check for a possible pulp exposure or caries prior to initiating extensive work.

The use of the invention enables one to monitor a patient's dental health. As with annotating dental diagrams in a conventional manner to record observed conditions and treatment, the observed resistance readings can be recorded. Subsequent readings are then compared to previous or baseline readings recorded in the patient's chart. What the resistance display means, those readings obtained from the scale located on the machine and can be, for convenience and reference, be noted in the patients' record.

Recording of resistance readings will aid the practitioner in monitoring the progression of decay. In addition to noting the progress of decay, the thickness of the enamel can be followed over a period of several years. Since a good thickness of normal enamel does not conduct electricity, as it becomes thinner and thinner, it is possible to begin to obtain readings that would indicate that the enamel thickness is less than acceptable. The practitioner may then decide if it is necessary to restore the tooth and those surfaces involved.

For differentiating between enamel, dentin, sclerotic dentin, reparative dentin, thin or weak dentin, carious pulp exposures, iatrogenic pulp exposures, perforations, major canals, accessory canals, cracks, fissures and craze lines, one would obtain resistance readings of the teeth or areas in question.

Areas of tooth or dental work that is intact will show high resistance which would be interpreted as intact enamel, sealed margins, no decay or breaks in the tooth structure. Readings obtained that allow the passage of some electricity (moderate resistance), but are intact and acceptable form of tooth structure. These low readings would be found when testing normal dentin, small cracks in the enamel that just penetrate the into the dentin, acceptable pin hole (pilot hole) locations in sound dentin, certain types of intact filling material including composite resins or cements, intact root surface, and tooth structure greater than 2 millimeters from the nerve.

Another class of conditions which give rise to medium to high audible readings (moderate to low measured resistance), includes deep decay, wet bases, near-perforation or thinned root walls, very close proximity to the nerve, pilot holes for pins that are beginning to encroach upon the nerve, cracks or fractures of significant depth, e.g., into the nerve.

A class of conditions which give rise to the highest audible reads, indicating lowest tooth resistance, includes conditions where little tooth structure remains such as frank pulp exposures (both carious and operator induced), cracks into the nerve, outright perforations of tooth structure, extra canals, uninstrumented canals, sclerosed canals that are so small as to miss clinical detection by use of explorer or magnification with a microscope.

The device may also be used to determine when a restoration material is cured. Restoration materials can be selected so as to take advantage of a resistivity change wherein the resistance of the material is lower when first prepared and applied, and the material undergoes an increase in resistivity as it cures.

For example, when a cavity is being removed and the tooth restored, the invention is initially used to locate the cavity and indicate when the decay has been fully eliminated. The invention is further used when the area being treated is filled with the restoration material by taking an initial resistance reading upon filling the cavity to establish an initial resistance value of the non-cured restoration material.

The inventive device is used to monitor curing of the restoration material by taking subsequent readings to observe the resistivity changes. When the resistance increases to a steady value, the material is largely cured. An important advantage of the invention is that the precise initial and final resistance values are not of critical importance as the practitioner can assess curing based on observing an initial lower resistance value and determining when the material is cured based on the resistance settling at an increased steady value.

This approach also applies to making a determination as to whether a filling material, base or cement had been adequately cured, dried, set or sealed, prior to conclusion of treatment. This method allows the practitioner, when making incremental additions of restorative material, to ensure each new incremental layer is fully cured prior to applying the next increment.

Although this aspect of the invention is applicable to any of the conventional restoration materials exhibiting the resistance change as a function of curing property, available dental materials should be selected with regard to conductance of electricity in the "wet" and "dried/set" or cured states. Material that may be considered for use in conjunction with this aspect of the invention are summarized below.

| Cement Type | State of Cement/Electrical Resistance ("R") | | |
|---|---|---|---|
| | Fresh Mix | Hardened on tooth | Hardened On Pad |
| ZnPO4 | Low R<br>Very High Audible | Moderate R<br>Low Audible | High R<br>No Audible |
| Poly-Carboxylate | Low R<br>Very High Audible | Low–Moderate R<br>Low–Medium Audible | High R<br>No Audible |
| Glass Ionomer | Low R<br>Very High Audible | Less Low R<br>High Audible | High R<br>No Audible |

An advantage of using the invention to evaluate curing is that it also provides a back-up evaluation of whether or not all the decay was in fact removed. With a properly restored tooth, once the restorative material cures, the resistance increases and no audible signal should be heard. However, on a tooth where some decay remains, even though the covering restorative material covers the decay and the restorative material has cure, there will remain will current conductive and hence an indication of remaining decay. Therefore, the practitioner is able to better access whether treatment has been successful, e.g., whether a canal or a crack has been sealed, and whether a perforation or a nerve exposure has been covered.

The present invention also finds application with the treatment of an isolated tooth area covered by a dental dam. The device can be used with a rubber dam or isolation of the area with cotton rolls as the device is unimpeded through the use of the rubber dam, provided a good connection of first monitor (lip clip) is made under the rubber dam. At times, isolation of the tooth with a rubber dam is the preferred method of isolation, because the laytex dam is not conducting (as are the laytex gloves worn by the operator) and hence can reduce the potential of a short circuit that would give a false positive reading.

With careful study, the device can be used to help diagnose a myriad of dental conditions or problems. As with any new technique attempted in medicine, the appropriate training in the usage and finer points of the technology is warranted. However, the invention provides the operator with a new approach to diagnosis, one that will enhance operator diagnosis and eventually treatment. In time, the usage will become second nature, as is the use of a dental handpiece, or the use and evaluation of dental x-rays. The device is intended to supplement the practitioner's repertoire of diagnostic aids, but in certain circumstances, may act as the primary source of information in a case.

Dentistry has undergone numerous changes over the years including the change from electrically driven handpieces to air driven turbine handpieces; from the use of amalgam filling to glass-based composite resin fillings. This dental diagnostic system and method would be no different. Given time, the practitioner would learn to use the device and parlay the extra information into his or her current treatment regime, and thus be able to make better decisions regarding potential treatment outcomes.

In certain procedures in dentistry, being able to make quick decisions and alter a course of treatment, almost instantaneously, is an acquired skill. Having years of practical clinically dentistry under one's belt is an advantage. However, having the aid of the device should allow practitioners to decide on treatment objectives and treatment modalities prior to commencement of treatment, or at the least, the ability to respond to various situations with a higher degree of confidence.

Patients are wary of the unknown, and having the means to communicate potential problems, side effects, deleterious situations, and being able to warn a patient, prior to embarking on a form of treatment, may lessen the possibility of poor communication. Often times, a patient's primary concern was not in how the treatment was rendered, but rather, they were not completely informed of the possible outcomes. Using the device to aid in diagnosis, and hence, being able to predict the possible outcomes, is certainly a benefit to any practitioner.

Since the system has many uses and is quite versatile, it may not be possible to go into detail on any given use, and the below are exemplarily. Experience in dentistry teaches us that for any given situation, there may be many different solutions; and there are, of course, as many different situations in dentistry as there are teeth. However, the field of endodontics appears to be very well suited for the use of the device. In addition to being able to locate hidden canals, or canals that are off the beaten trail, it is possible to locate canals that have been previously missed during root canal therapy. Quite often, a patient having sensitivity to cold or hot, or a having a periapical lesion along the side or end of the root with the same tooth that has been previously treated by root canal therapy, will have an uninstrumented canal. It is possible to gain access back into the previously completed root canal and search around with an endodontic explorer attached to the device, until an accessory canal is located. These canals are often in the MB2 location, but can be found in the DB2 position, or even as a palatal accessory canal, in upper molars for example. Of course, familiarity with nerve morphology would yield similar finds in the other teeth in the mouth.

Although commercially available sealing cements for gutta percha are not specifically designed, at this time, to have conduction/non-conduction properties, it is possible to verify the complete seal of a completed root canal using such cements. There are some cements on the market today that inadvertently have such qualities, but are used on a limited basis in endodontics at this time, and not specifically for this purpose. One could test a tooth for adequate seal at the completion of root canal therapy, and record these findings in the patient's chart. At some future date, if needed, the tooth could be opened up, and tested again. If there is any change in the readings, coupled with a patient complaint of sensitivity of some sort, the canal suspected of leakage, or bacterial infiltration could be cleaned again. It may be possible to pinpoint the exact problem, without the necessity of total retreatment of the case. If treatment time could be lessened or reduced, the doctor's time could be freed up to go onto the next case. This is not to say the any practitioner should "cut corners" on any treatment, but rather to point out that the possibility for improved diagnostics is possible. With the demand for improved endodontic therapy on the rise, coupled with the fact that the general population has more teeth today than sixty years ago, dentistry will undoubtedly need to change just to keep up with demand. We now see some practitioners completing root canal therapy in one visit. Just a mere twenty years ago, this would have been unheard of, and actually frowned upon. But times are changing, and dentistry must change with them.

The technique of performing root canal therapy can be frustrating at times; each case is just a little bit different from the next. With the aid of the device, it is possible to determine if a canal is sealed through a dentinal plug. The dentinal plug can be made up of debris from dentinal filings or other amorphous material. It may occur by accident or through design. However, these dentinal plugs can make a tight seal in the apex of a tooth, and be as secure as the standard gutta percha seal with cement. The canal can be tested for the presence of a dentinal plug by placing a file attached to the device into the canal in question. In the case where no readings are obtained, especially in a canal where readings were previously possible, the canal is mostly clogged with the plug. The plug will generally not pass electricity. The practitioner would then need to decide if he or she should spend the time required to extirpate the plug, or whether the plug can be used as the actual seal.

There are numerous iatrogenic (dentist caused problems or mistakes) results to contend with in endodontics. Some are quite major such as perforations, and others are smaller in nature. Separated or broken files can be of concern during treatment. Most dental practitioners performing root canal therapy on a regular basis can attest to broken files. The instruments are small in nature, and can fracture quite readily if proper care is not taken. The device can aid the practitioner in locating exactly where the separated instrument is lodged. By carefully placing a new file into the canal, while hooked up to the invention, the practitioner can slowly lower the file into the canal. Once contact is made with the broken instrument, a increase in readings should be obtained. At that point, the practitioner may decide whether to drill open the canal further to facilitate grabbing the piece, or whether to work around the instrument down to the apex, or whether to leave the piece alone. Incidentally, if the canal no longer gives any readings at all, it may be possible that a dentinal plug is present below the separated instrument. Should this be the case, the operator would then decide on whether to leave the root/canal alone, since dentinal plugs can lead to an acceptable result. Of course, the patient would be advised of the situation, and recalled on a regular basis for follow-up, and treatment if necessary.

Roots and canals in roots may be found to curve in all sorts of unusual directions at the apex. In fact, most normal anatomy of a nerve is quite twisted with accessory canals coming off the main branch at any given level. Should the need arise, the practitioner can attempt to locate the exact direction of curvature of a dilacerated (twisted or excessively curved) root apex. By inserting a small file while attached to the invention, into a dried root end, and by carefully rotating the file, various reading will be realized. The readings will become higher as the file comes closer to the direction of the curve. By carefully filing in that direction, the operator should be able to negotiate the last portion of the root tip. Complete filing to the apex, or about 1 mm shy of the apex, is fairly standard in dentistry today. However, the curve of the root tip may appear 1–3 mm away from the anatomical end of the tooth. Having the ability to diagnose and negotiate this part of the root can aid in increasing the success rate of root canal therapy.

In making the determination if a crack is present on or within the tooth, the operator will find that moving the dental tool across the exterior surface while observing for a change in audible tone of the speaker or a yellow or red LED light to become activated, will indicate a change in the resistance or quality of the tooth or area of the tooth being tested. Such a change when testing the enamel or root structure of the tooth would indicate a crack in the structure. Other possible causes for a change in the resistance of the tooth might mean decay, thinned enamel, leakage of a filling, marginal breakdown.

In the case of a crack, the solid enamel is the hard outer casing of a tooth and normally has a very high resistance, greater than 650K ohms. For all intents and purposes, this is an infinite resistance. This means that under ideal circumstances, enamel will not allow electricity to flow through it.

However, if the enamel has a crack through it, moisture, debris, bacteria, foodstuffs and the like will invariably be found in the crack. This "moisture" will allow for the transmission of electrical current through the enamel. The amount that travels through the enamel, through the tooth and patient's body, and through the negative lead, will be measured and indicated by the device.

Of particular concern in making the diagnosis of a cracked tooth or root, is the poor prognosis involved. With current dental technology, the success rate for salvaging teeth with cracks in them is very low. However, it may be possible for the practitioner to seal up a crack with cement or other non-conducting sealing agent. After hardening of the cement or sealing agent, the area in question can be tested again. Low or no readings may indicate that the crack is sealed as well as possible. Of course, the patient would still be advised to the nature of the problem, and given the option of extraction of the tooth.

Nerve tissue plays a vital role in teeth. It tells us from a young age what we can and cannot do. It advises us when something is not right, such as decay, recession, over-use and the like. However, nerves can be tricky to treat, and even trickier to save. Additional use of the invention involves the outlining of the nerve in order to protect it from thermal or other irritating factors. Although the general trend in dentistry seems to be getting away from nerve protection, it is a fairly simple matter to use the invention to outline and protect a nerve. By attaching the device to a dental explorer or even a dental handpiece, one may get an idea of the size and shape of the nerve, and an idea of it's proximity to the base of the preparation, by running the probe over various areas of the tooth structure. Readings become more obvious when remaining dentin approaches 2 mm or less, and thus, in these areas where the readings are more prominent, the dentist might choose to place a calcium or other suitable base material. Once the material has fully set (provide it is a non-conducting material of course) the area can be tested again. Lower readings would indicate a layer that now will aid in protection of the nerve. The tooth could then be filled in a suitable manner, with the hopes that the nerve would both heal and be protected at the same time. Since a nerve that will not heal may require root canal therapy, the operator should make every effort to help the tooth heal properly. Anything less would be an oversight (to say the least) on the part of the operator.

In addition to determining the whereabouts of a nerve, the dentist may also be able to determine the type, and quality of tooth structure present. Since all tooth structure passes electricity of varying amounts, it is possible to determine the resistive qualities of the tooth structure being tested. Once the resistance is known, a type of tooth structure can be ascertained. For instance, good/solid enamel passes little or no electricity (see chart); good quality dentin passes some electricity and hence has a lower resistance than that of enamel. Various types of dentin can be found due to the differences in the ability to pass electricity. There is sclerotic dentin, reparative dentin, dentinal bridges, and even combinations in various areas. By knowing what type of dentin is present, the operator can decide if it should be treated in any way.

Having the ability to check enamel prior to bonding brackets would be helpful to any orthodontist. In the event that poor quality enamel is present, or if it is determined that enamel does not exist, then the orthodontist might elect to work around the problem by choosing a different location for bonding a bracket. The device will also indicate if a filling is present. In certain circumstances, it may be difficult to visually determine if a filling is present on the surface to be bonded. With the advent of superior cosmetically oriented restorative filling materials, the filling may be difficult to discern from naturally occurring tooth structure. By placing a probe onto the tooth surface, any less than adequate structure, such as thinned enamel, or a filling, may be discernable.

Once the bracket is bonded in place, the general dentist may periodically check the tooth surface around the bracket to ensure that it is not becoming carious. Should the device begin to exhibit higher readings, the dentist may elect to further investigate the area. Any decay, of course, would be attended to, and the patient may be informed that removal of a bracket, which is situated upon filling material or less than adequate enamel, might fracture or become dislodged upon removal of the bracket.

The present invention is suitable for modification within the scope of the invention. Certain "bells and whistles" could be added without changing the basic concepts and usage of the invention. It may be possible to reverse engineer some commonly used dental equipment so as to incorporate the invention.

It is anticipated that a great change in dentistry would be the adaptation or change in materials to supplement the device. At the current time, some materials have been found to aid in the function of the device. The chart included outlines some of the characteristics of various cements, and their conductive capacities. However, the properties noted are probably more by coincidence than design by the manufacturers. The scope and breadth of the possibilities in dental materials, as related to the device, is quite tremendous. They range from protective bases, to cements, to filling materials, to sealing agents. All of which would capitalize on the conductive properties in wet and dry states.

The invention may be used on a fully anesthetized patient. Due to the action potential of a nerve, the depolarization of the membrane occurs at around 75 millivolts. It is possible that certain patient's action potential may be lower than that due to nerve injury, bacterial infiltration, or genetic and/or random occurrence. The patient should be fully anesthetized prior to use of the device. A further improvement in design might allow for decreasingly smaller amounts of voltage to be passed through the tooth, in this regard, perhaps the patient would not even need to have anesthesia. However, the invention may serve as a pulp tester on a non-anesthetized patient, or to determine if the applied anesthesia has taken effect. It is noteworthy to mention that a certain phenomena that could be termed "plurality of physiological resistor circuits" seems to hold true with teeth. Any conducting medium placed or found within the tooth can act as a multi-conduit for electrical flow. More specifically, amalgam filling material, extensive decay, and gold, for instance, allow for multiple pathways through which electricity may flow. Care must be exercised that the phenomena be taken into account.

Figure 7:
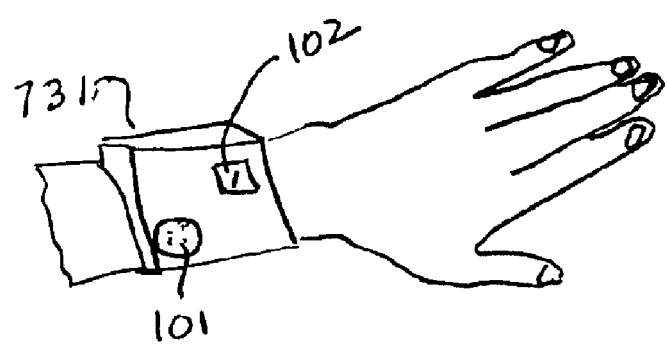
FIG. 7 shows an embodiment of the invention with the resistance indicating means attached to the operator's wrist.

FIG. 7 shows an embodiment of the invention where the resistance indicating means is of miniaturized circuitry housed in a wrist-watch size case 731 the operator's wrist. Alternatively, the case 731 could be attached to the operator's arm. The dental tool comprises wireless technology wirelessly connecting the dental tool to the indicating means.

Although these preferred embodiments have been disclosed, the invention is not limited and includes equivalents and obvious variations.

I claim:

1. A method of dental diagnosis comprising the steps of:
   exploring a tooth surface or tooth material of a patient with a dental tool applying a known DC voltage to a localized region of the tooth surface area to locate a treatment area indicated by either a local lower resistance area surrounded by a higher resistance area, or a local higher resistance area surrounded by a lower resistance area;
   allowing for the assimilation of additional information needed for advanced treatment of the area being tested;
   verifying successful treatment of the treatment area by applying the dental tool with the known DC voltage to the treatment area and confirming the presence or absence of the local lower or higher resistance area; and
   permitting continuation of testing of the treatment area or a new treatment area, based upon those new findings.

2. The method of claim 1, wherein the information received through use of the device will improve the diagnostic capabilities currently in use in dentistry, in a new an innovative manner.

3. The method of claim 1, wherein there is obtained adjunctive information through which a better decision making process for treatment of teeth is realized.

4. The method of claim 1, wherein there is obtained periodic monitoring during treatment, allowing for correction and improved analysis of teeth, materials and tooth related structures during treatment.

5. The method of claim 1, wherein there is obtained information that will facilitate communication of findings from the operator to the patient.

6. The method of claim 1, comprising the further step of moving the dental tool across the floor of an opened tooth pulp chamber while observing for a change in tooth resistance to indicate the presence of a major canal orifice,
   wherein said canal orifice is indicated by a low tooth resistance in a localized area.

7. The method of claim 1, comprising the further step of moving the dental tool across the floor of an opened tooth pulp chamber while observing a change in tooth resistance to indicate the presence of a minor or accessory canal orifice,
   wherein said canal orifice is indicated by a low tooth resistance in a localized area.

8. The method of claim 1, comprising the further step of moving the dental tool across the floor of a previously completed root canal while observing a change in tooth resistance to indicate the presence of a uninstrumented or previously missed canal orifice,
   wherein said canal orifice is indicated by a low tooth resistance in a localized area.

9. The method of claim 1, comprising the further step of moving a dental tool across a sealed canal while observing a change in local resistance to indicate the quality of the seal of a canal.

10. The method of claim 1, comprising the further step of placing a dental tool into a canal to determine the presence or absence of a dentinal plug,
    wherein said dentinal plug is indicated by an extremely high tooth resistance in the localized canal.

11. The method of claim 1, comprising the further step of using said device to locate a broken or separated file within a tooth canal by placing a dental file into a canal while monitoring the local resistance change while proceeding down the canal, wherein the broken file will be indicated by a sharp change in local audible reading.

12. The method of claim 1, further comprising the steps of locating the direction of curvature of a root apex by:
   placing an endodontic file with the tip bent at a 45 degree angle into a tooth canal and carefully proceeding toward the root apex until the file meets with obstruction;
   rotating the file slowly in a clockwise or counterclockwise direction while monitoring the local resistance and audible readings;
   stopping the rotation of the file at the point at which the localized readings or audible readings are the highest;
   withdrawing the file without further rotation to ascertain the direction of curvature of the canal, and;
   verifying the direction of curvature by continuing to instrument the canal to the root apex in same direction as indicated by the device.

13. The method of claim 1, comprising the further step of testing for an adequate seal of a crack or hole by placing a non-conducting cement over the crack or hole and testing for a new high localized resistance by moving the dental tool over the sealed area once the cement has cured.

14. The method of claim 1, further comprising locating the size, shape and extent of a pulp chamber roof or nerve outline by moving a dental tool across the base of a preparation while observing a change in local resistance,
   wherein a high reading indicates a close proximity to the nerve and a low reading would indicate a further distance from the nerve.

15. The method of claim 1, comprising the further step of covering the nerve with a protective non-conducting base and reassessing the protection of the nerve by moving the dental tool across the base of the preparation while observing a change in local resistance,
   wherein lower readings indicates adequate nerve protection.

16. The method of claim 1, comprising the further step of moving the dental tool over dentin while observing the changes in local resistance to identify the type of dentin present,
   wherein a differentiation is made between sclerotic dentin, reparative dentin, dentinal bridges and other types of dentin based upon the variations in local resistances.

17. The method of claim 16, comprising the further step of moving a dental tool across a tooth surface prior to attachment of an orthodontic bracket or band and observing the changes in local resistance,
   wherein high readings indicate poor quality tooth structure or the presence of a filling material.

18. The method of claim 1, comprising the further step of placing a dental tool on a tooth surface prior to, or after the administration of local anesthesia, and observing the patient's reaction,
   wherein said observation indicates the sensitivity of a tooth nerve or level of anesthesia.

19. A dental diagnostic system, comprising:
   a tooth condition analyzer having
   a DC voltage source;
   a positive voltage terminal providing a connection terminal to a dental tool and for applying a known, fixed-level DC voltage onto the dental tool;
   a negative voltage terminal providing a connection terminal to a return connector for completing a circuit from the DC voltage applied to the dental tool via a patient's tooth;
   a voltage circuit connected to said positive and negative voltage terminals and providing the known, fixed-level DC voltage across said positive and negative voltage terminals; and
   a resistance indicating means operatively connected to said positive and negative voltage terminals for sensing a current flowing therebetween and converting the current to a resistance indication,
   wherein said voltage circuit limits the current between said positive and negative voltage terminals to 300 microamps,
   said resistance indicating means is of miniaturized circuitry housed in a wrist-watch size case designed to be attached to the operators wrist or arm, and
   the dental tool comprises wireless technology wirelessly connecting the dental tool to the indicating means.

20. the system of claim 19, further comprising
   a base unit/computer for patient record keeping wireless connected to said dental tool.

* * * * *